United States Patent [19]

Love et al.

[11] Patent Number: 5,755,782
[45] Date of Patent: *May 26, 1998

[54] STENTS FOR AUTOLOGOUS TISSUE HEART VALVE

[75] Inventors: Charles S. Love; Jack W. Love, both of Santa Barbara; John H. Calvin, Carpenteria, all of Calif.

[73] Assignee: Autogenics, Glasgow, Scotland

[ * ] Notice: The term of this patent shall not extend beyond the expiration date of Pat. No. 5,423,887.

[21] Appl. No.: 169,336

[22] Filed: Dec. 17, 1993

Related U.S. Application Data

[60] Continuation-in-part of Ser. No. 925,380, Aug. 3, 1992, Pat. No. 5,423,887, which is a division of Ser. No. 646,001, Jan. 24, 1991, Pat. No. 5,163,955.

[51] Int. Cl.$^6$ ............................................. A61F 2/24
[52] U.S. Cl. ...................................... 623/2; 623/900
[58] Field of Search ...................... 623/2, 900; 24/484, 24/567

[56] References Cited

U.S. PATENT DOCUMENTS

| | | |
|---|---|---|
| 1,266,423 | 5/1918 | Denise ........................... 24/484 |
| 2,708,950 | 5/1955 | Averett ........................ 24/567 X |
| 2,822,819 | 2/1958 | Geeraert . |
| 3,022,802 | 2/1962 | Lewis . |
| 3,532,016 | 10/1970 | Lane . |
| 3,548,418 | 12/1970 | Angell . |
| 3,570,014 | 3/1971 | Hancock . |
| 3,714,671 | 2/1973 | Edwards et al. . |
| 3,755,823 | 9/1973 | Hancock . |
| 3,824,140 | 7/1974 | Hofmann . |
| 4,035,849 | 7/1977 | Angell et al. . |
| 4,084,268 | 4/1978 | Ionescu et al. . |
| 4,106,129 | 8/1978 | Carpentier et al. . |
| 4,172,295 | 10/1979 | Batten . |
| 4,192,020 | 3/1980 | Davis et al. . |
| 4,247,292 | 1/1981 | Angell . |
| 4,297,749 | 11/1981 | Davis et al. . |
| 4,388,735 | 6/1983 | Ionescu et al. . |
| 4,427,470 | 1/1984 | Kolff . |
| 4,441,216 | 4/1984 | Ionescu et al. . |
| 4,470,157 | 9/1984 | Love . |
| 4,478,661 | 10/1984 | Lewis . |
| 4,490,859 | 1/1985 | Black et al. . |

(List continued on next page.)

FOREIGN PATENT DOCUMENTS

| | | |
|---|---|---|
| 0179562 | 7/1989 | European Pat. Off. . |
| 0766025 | 6/1934 | France ........................... 24/484 |
| 2337543 | 8/1977 | France . |
| 1116573 | 7/1985 | U.S.S.R. . |
| 1189399 | 4/1970 | United Kingdom . |
| 1264471 | 2/1972 | United Kingdom . |
| 1264472 | 2/1972 | United Kingdom . |
| WO 91/15167 | 10/1991 | WIPO . |

OTHER PUBLICATIONS

The Autogenous Tissue Heart Valve: Current Status; Charles S. Love, B.A. and Jack W. Love, D. Phil., M.D., vol. 6, No.4, 1991; Journal of Cardiac Surgery, pp. 499–506.

(List continued on next page.)

Primary Examiner—David H. Willse
Attorney, Agent, or Firm—Knobbe, Martens, Olson & Bear, LLP

[57] ABSTRACT

An improved set of stents for autologous tissue heart valves is provided. The stents are designed with the aid of a computer-aided-design (CAD) system, and nest within each other to securely clamp a piece of tissue which forms the leaflets of the heart valve. The geometrical features of the stents are designed to provide uniform nesting between the stents to prevent the formation of stress raisers on the tissue. Additionally, the windows in the stent posts are narrowed to prevent the suturing needle used during implantation of the valve from becoming lodged in the garter springs which clamp the outer stent to the inner stent. Finally, the sock covering the outer stent is bonded to the stent base at both upper and lower locations to isolate the bonds from the patient's blood flow.

7 Claims, 8 Drawing Sheets

U.S. PATENT DOCUMENTS

| | | |
|---|---|---|
| 4,501,030 | 2/1985 | Lane . |
| 4,512,471 | 4/1985 | Kaster et al. . |
| 4,597,767 | 7/1986 | Lenkei . |
| 4,605,407 | 8/1986 | Black et al. . |
| 4,687,483 | 8/1987 | Fisher et al. ............................. 623/2 |
| 4,725,274 | 2/1988 | Lane et al. . |
| 4,838,288 | 6/1989 | Wright et al. . |
| 4,851,000 | 7/1989 | Gupta . |
| 5,036,312 | 7/1991 | Lester .................................... 340/679 |
| 5,037,434 | 8/1991 | Lane . |
| 5,060,716 | 10/1991 | Heine ................................... 24/567 X |
| 5,147,391 | 9/1992 | Lane ........................................ 623/2 |
| 5,163,955 | 11/1992 | Love et al. .............................. 623/2 |
| 5,197,979 | 3/1993 | Quintero et al. . |
| 5,326,370 | 7/1994 | Love et al. . |
| 5,326,371 | 7/1994 | Love et al. . |
| 5,423,887 | 6/1995 | Love et al. .............................. 623/2 |
| 5,488,789 | 2/1996 | Religa et al. ......................... 38/102.2 |

OTHER PUBLICATIONS

Love, et al., "Pericardial Tissue as a Cardiac Valve Substitute—Proceedings of a Symposium", Thumersbach, Austria, Sep. 1988, pp. 1–221.

"Rapid Intraoperative Fabrication of an Autogenous Tissue Heart Value: A New Technique", Love et al., Proc. of the Third Internatioanl Symposium on Cardiac Bioprosthesis, Yorke Medical Books, New York, NY 1986. pp. 691–698.

"Frame–mounted Tissue Heart Valves: Technique of Construction", Bartek et al., Dept. of Cardiothoracic Surgery, The General Infirmary at Leeds and Leeds University, Thorax (1974), 29, 51–55.

"Doppler and Hemodynamic Characteristics of the Autogenics Bioprosthetic Valve", Khan et al.

"A Fascia Lata Mitral Valve Based on the 'frustum' principle", Brownlee et al., Guy's Hospital, London, Thorax (1971), 26, 284.

"The Flexible Stent", Reis et al., reprint from The Journal of Thoracic and Cardiovascular Surgery, vol. 62, No. 5, pp. 683–689, Nov. 1971.

"A method for preparing and inserting a homograft aortic valve", Barratt–Boyes, Brit. J. Surg, 1965, vol. 52, No. 11, Nov. pp. 847–856.

"In Vitro Testing of Bioprostheses", Reul et al., vol. XXXIV Trans Am Soc Artif Organs, 1988.

STENTS FOR AUTOLOGOUS TISSUE HEART VALVE

This application is a continuation-in-part of U.S. application Ser. No. 07/925,380, filed Aug. 3, 1992, now U.S. Pat. No. 5,423,887, which is a division of U.S. application Ser. No. 07/646,001, filed Jan. 24, 1991, now U.S. Pat. No. 5,163,955.

BACKGROUND OF THE INVENTION

This invention relates to the fabrication of bioprosthetic heart valve replacements. Valve replacements are required for patients having a heart valve which is diseased or otherwise incompetent. Commonly, heart valve bioprostheses are made from a combination of animal tissue and mechanical elements. These bioprostheses have an advantage over purely mechanical valves in that they do not require the use of anticoagulant therapy that plagues purely mechanical valves.

U.S. Pat. No. 5,163,955 (the '955 patent) discloses such a bioprosthetic valve, in which an inner stent, on which the tissue used to construct the valve is wrapped, is inserted into a spreadable outer stent containing a self-adjusting tensioning spring around the circumference of its base. The inner stent posts are fitted with a plurality of outwardly-projecting pegs which register with holes cut in the tissue, and the inner stent assembly is covered with cloth. The spread outer stent clamps the stents together at its base and at a plurality of posts projecting from the bases of both the inner and outer stents. This clamping thus secures the tissue while compensating for irregularities and supplying a clamping force which is evenly distributed over the entire circumference of the tissue.

The outer stent disclosed in the '955 patent has an annular base constructed with a groove around its circumference, into which a self-adjusting tensioning means such as a garter spring is fitted. The garter spring provides a clamping force when the inner stent is inserted into the outer stent. Additionally, the posts on the outer stent are configured with windows surrounded by struts, which give shape to the post. The window is shaped to conform to the shape of the inner stent posts while leaving a small gap between the inner stent posts and the struts when the inner stent is inserted into the outer stent. Such an arrangement facilitates the insertion of the inner stent into the outer stent and provides for a uniform application of the clamping force to the tissue.

At the bottom of each of the windows in the outer stent posts are slots which segment the base into a plurality of arcuate portions. The slots enable the outer stent to be spread open so that it can easily be fitted over the inner stent without damaging the tissue during the valve assembly process.

An elastomeric sewing ring is bonded to the base of the outer stent assembly to facilitate the sewing of the assembled heart valve into the patient. The entire assembly is covered with a fabric cover, typically made out of DACRON, which is bonded to the bottom of the outer stent base.

SUMMARY OF THE INVENTION

In accordance with the present invention, an improved outer stent is provided for a heart valve for securing an inner stent with a base and a plurality of posts extending and spaced around the base and having tissue wrapped thereon. The inner and outer stents cooperate to form a heart valve implanted into a patient, typically by the use of sutures.

The outer stent has a base including a plurality of slots and preferably two tensioning springs disposed around the circumference of the base to prevent the inner and outer stents from becoming unsecured if one of the springs breaks. The provision of more than one tensioning spring is an advantageous feature of the present invention which gives the valve redundancy, for if one spring breaks, another will continue to provide the outer stent's clamping force on the inner stent.

Additionally, the slots around the outer stent base are advantageously fashioned to be narrow enough to decrease the potential for the suturing needle becoming entangled in the tensioning springs during the insertion procedure. Their width is selected to be the minimum sufficient to allow the outer stent to supply an adequate clamping force if a small amount of tissue or debris becomes lodged in the slot.

The outer stent has a plurality of posts extending upwardly from its base connected to each other by scalloped portions and registering with the inner stent when the inner and outer stents are secured together. The posts each include a window to allow the registry of the corresponding inner stent posts with the outer stent. A further advantageous feature of the present invention is the provision of a wedge-shaped elastic ring bonded to the base of the outer stent to provide a better fit for the valve in the patient's aortic root.

The geometry of the inner and outer stents is determined using three basic parameters, the inner stent post width, the height of the scallops on the inner stent connecting its posts, and the inner diameter of the valve. These parameters are chosen based on the size required of the heart valve to be replaced. The chosen values for these parameters are then input into a computer-aided design (CAD) software package, which utilizes curve-fitting algorithms to generate three-dimensional surfaces corresponding to the inner stent blank. Next, the outer stent geometry is derived from the curves developed during computation of the inner stent geometry. An important object of the outer stent geometry computation process is the provision of sufficient clearance between the inner and outer stents at all points to prevent the tissue from being too tightly clamped and forming stress raisers which increase the chances of fatigue tearing of the tissue.

The outer stent assembly is typically molded out of DELRIN or another suitable thermoplastic and is covered by a fabric sock, typically of DACRON. In the preferred embodiment of the present invention, the sock is attached to the stent by first bonding it to the bottom surface of the base of the outer stent at a first weld, then wrapping the covering around both the outer and inner surfaces of the outer stent, covering the base of the outer stent a second time, and finally securing the other end of the sock to the top of the outer stent base with a second weld. This method of construction is a significant feature of the present invention, since it provides two layers of fabric around the outside of the base of the outer stent. The outermost layer of fabric covers the first weld and thus keeps it out of the patient's bloodstream, thereby preventing blood clots from forming on the weld and entering the patient's bloodstream. The extra layer also provides increased strength for the valve base assembly by virtue of the double thickness it imparts to the cloth covering.

Along the segments where the fabric covers the slots in the stent, the two layers of fabric covering the outer stent base are advantageously bonded together with a suitable adhesive. This is done to prevent a tunnel from forming between the layers at points over the slots in the base; such a tunnel could serve as the formation point for blood clots.

The stent of the present invention therefore achieves the objects of providing a reliable securing force for the tissue mounted on the inner stent of a bioprosthetic heart valve while minimizing insertion difficulties and preventing the formation of blood clots.

DETAILED DESCRIPTION OF THE PREFERRED EMBODIMENTS

Figure 1:
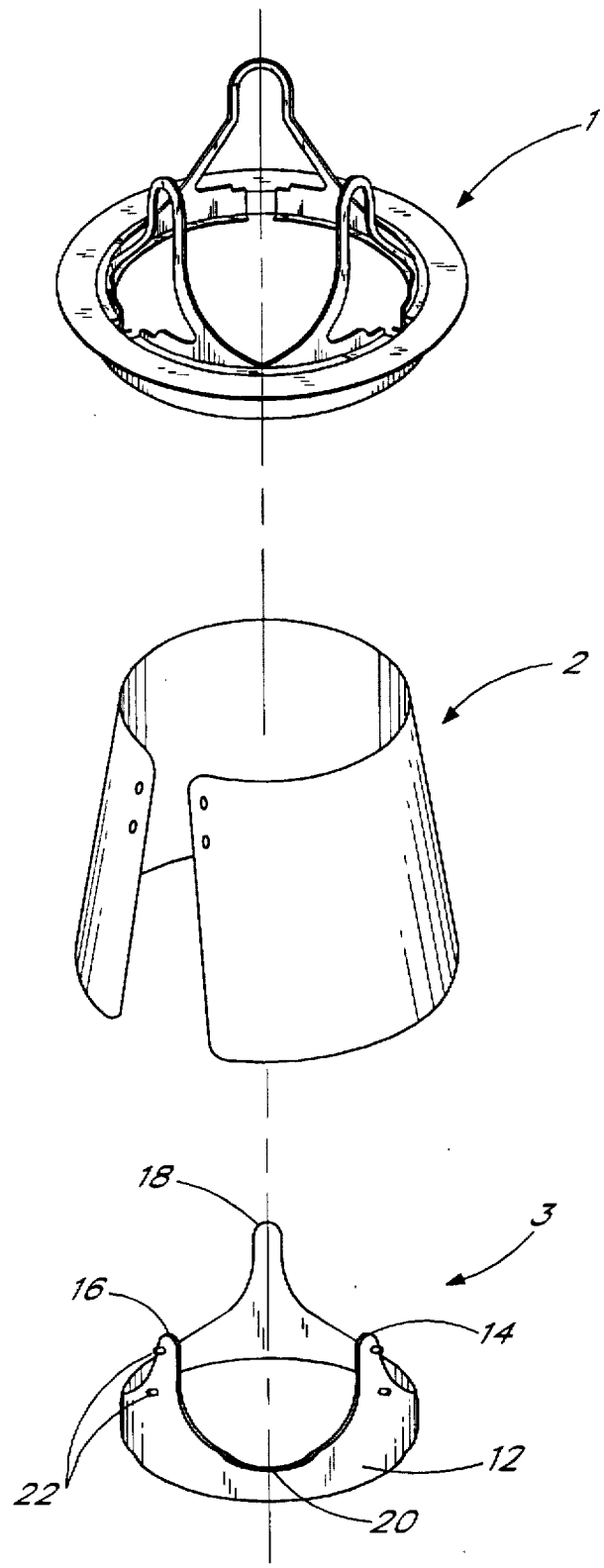
FIG. 1 is a perspective view of the major components in the valve assembly.

The components which make up the assembled valve are illustrated in FIG. 1. As illustrated, these components include outer stent 1, tissue 2, and inner stent 3. The inner and outer stents have frames, respectively constructed out of a thermoplastic such as DELRIN or the like using injection molding to form the entire component using unibody construction techniques, instead of welding or the like to attach any protuberances. Unibody construction is less risky to the patient than welding, since welded bonds can break more easily, leading to the injection of valve components or fragments into the bloodstream.

Once constructed, the outer stent frame is integrated with other components, including a sewing ring and a plurality of garter springs or similar tensioning members, and both frames are covered with a fabric such as DACRON or the like, to form the completed inner and outer stents used in the valve assembly.

The inner stent frame is preferably constructed with an annular base 12 with three posts 14, 16, and 18 extending from the annular base along the axis of the valve in the direction of blood flow through the valve. Preferably, three such posts are spaced uniformly around the annular base, i.e. such that the centers of adjacent posts are separated by 120 degrees on a circle passing through all three. The posts are connected by scalloped walls, such as that illustrated at 20. The posts are configured with a plurality of outward-facing members 22. These members are later shaped into tissue alignment members for use in holding the tissue in place while the valve is being assembled. Finally, the inner stent is covered by a fabric sock made of DACRON or a similar material, the sock being secured by bonding to the base of the inner stent.

Figure 5:
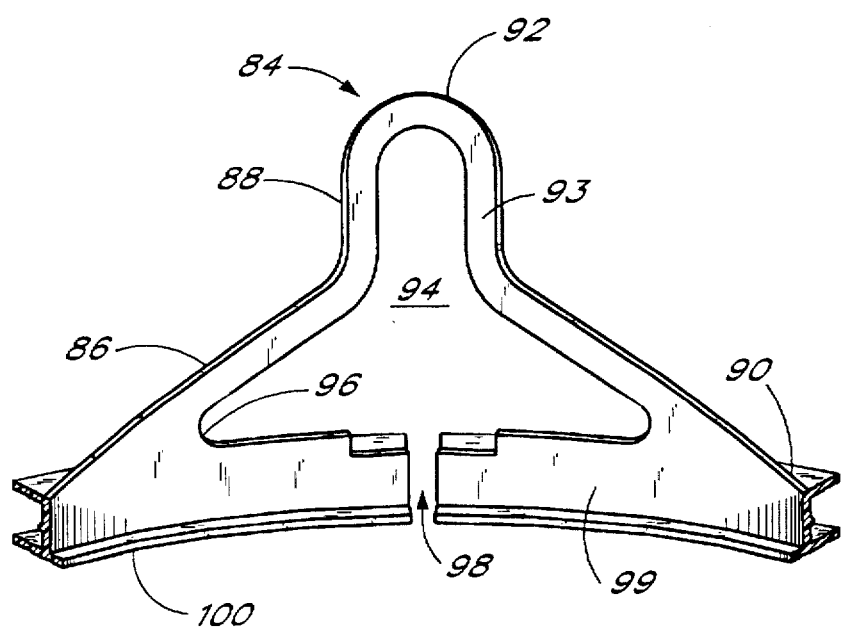
FIG. 5 is a partial cross-sectional view of a portion of an outer stent of the present invention.

Referring to FIG. 5, the outer stent 1 has a base 99, from which rise scalloped edges 90, which separate the outer stent posts, such as that shown at 92. The post 92 includes a strut 93 and has a window 94 cut out of it for receiving an inner stent post. At the bottom of the window are fillets 96 and slots 98 segmenting the base of the outer stent into arcuate portions, such as 100. An important advantage of the present invention is that the slots 98 are made as thin as possible to minimize the risk that the sutures used in implanting the valve in the patient will become entangled in the securing springs located around the base of the outer stent. However, if the slots are made too thin, they may pinch the tissue and prevent the outer stent from supplying the clamping force necessary to hold the inner stent in place. In practice, it has been found that a width of 0.050 inches is satisfactory clearance. This width is approximately equal to twice the sum of the tissue and cover thickness.

The tissue 2 is preferably taken from the patient during the surgical procedure, and is preferably pericardium. However, other types of tissue, such as autologous fascia lata or animal or cadaver tissue, may also be used as well. After being harvested from the patient, the tissue is immersed in a weak glutaraldehyde solution for a brief period of time, and is preferably cut into the proper shape using a die described in the '955 patent, which is fully incorporated herein by reference. The current assignee's co-pending application, Ser. No. 08/169,620, filed Dec. 17, 1993, discloses an improved tissue cutting die, and is also incorporated herein by reference. The use of other means of cutting the tissue, such as a scalpel, is also possible.

The completed valve is assembled by wrapping the tissue 2 around the inner stent 3, spreading open the outer stent 1, and inserting the inner stent into the outer stent. A technique and tools for performing this operation are disclosed in the present assignee's application Ser. No. 08/238,463, filed Dec. 17, 1993, and incorporated fully herein by reference.

The design of the inner and outer stents must achieve several important objectives. Firstly, the inner and outer stents should remain slightly separated from each other when mated. If they do not, the tissue wrapped on the inner stent will be pinched by the outer stent at the locations where they have insufficient separation, potentially resulting in fatigue tearing and failure of the tissue. Secondly, the tissue wrapped around the inner stent should form three spherically-shaped cusps to distribute the stresses of closure as evenly as possible over the valve. Finally, the inner stent scallops on which the tissue rests should have a horizontal profile to prevent the formation of stress raisers at the points of contact between the tissue and the scallops.

The outer and inner stents are designed with a complex, three-dimensional shape corresponding to the desired valve size in order to achieve these goals. The design is preferably carried out on a computer using computer-aided design (CAD) software having the capability to represent three-dimensional objects. As described below, in the preferred embodiment, the designer first creates a basic geometry for the stents and uses this to define the scallop geometry. This scallop geometry is used to split a rotational surface created to define the stent blank, creating the proper shape for the stent in three dimensions. Necessary surfaces and fillets are finally added to this shape to create the final stent shape. This shape is then input into machine tooling which cuts an electrode into the corresponding shape. Finally, the electrode is used to dissolve a pattern into a block of a suitable metal, such as a nickel-steel alloy, into the final mold for injection-molding the stents.

The basic geometry of the inner stent 3 is determined by three parameters dependent on the size and strength of the valve desired, namely the post width, the scallop height above the base, and the inner diameter of the valve. The post width is determined from the strength desired for the inner stent and the requirement that the completed valve fully close. The post must be made wide enough to give the inner stent sufficient strength but must not be made so wide that the amount of tissue draped over the inner stent posts is so great that the valve cannot properly close. Representative values for this dimension which have been found acceptable in practice for variously-sized valves are given in column K in Table 1.

The scallop height must be sufficient to achieve three objectives: (1) allow the leaflets of the valve to completely close, (2) provide sufficient flexibility to absorb the shock of valve closure, and (3) distribute the stresses encountered during normal use of the valve evenly throughout the tissue leaflet area. The choice of the inner diameter of the valve is based on the size of the patient's annulus, as measured during the surgical procedure with an obturator such as that disclosed in the present assignee's pending application Ser. No. 08/169,618, filed Dec. 17, 1993, which is incorporated by reference herein. Values for the scallop height as a function of inner diameter which have been determined to be satisfactory in practice can be determined by subtracting dimension D in Table 1, which is the distance from the scallop base to the top of the inner stent posts, from the height of the inner stent, shown as dimension E in Table 1.

An important advantage of the design methodology of the present invention is that it allows the use of a single method to easily fabricate size-specific stent kits corresponding to varying annulus diameters. The parameters associated with each annulus diameter are easily input into the computer-aided design (CAD) software, which generates a corresponding stent geometry while requiring little user input.

Figure 2:
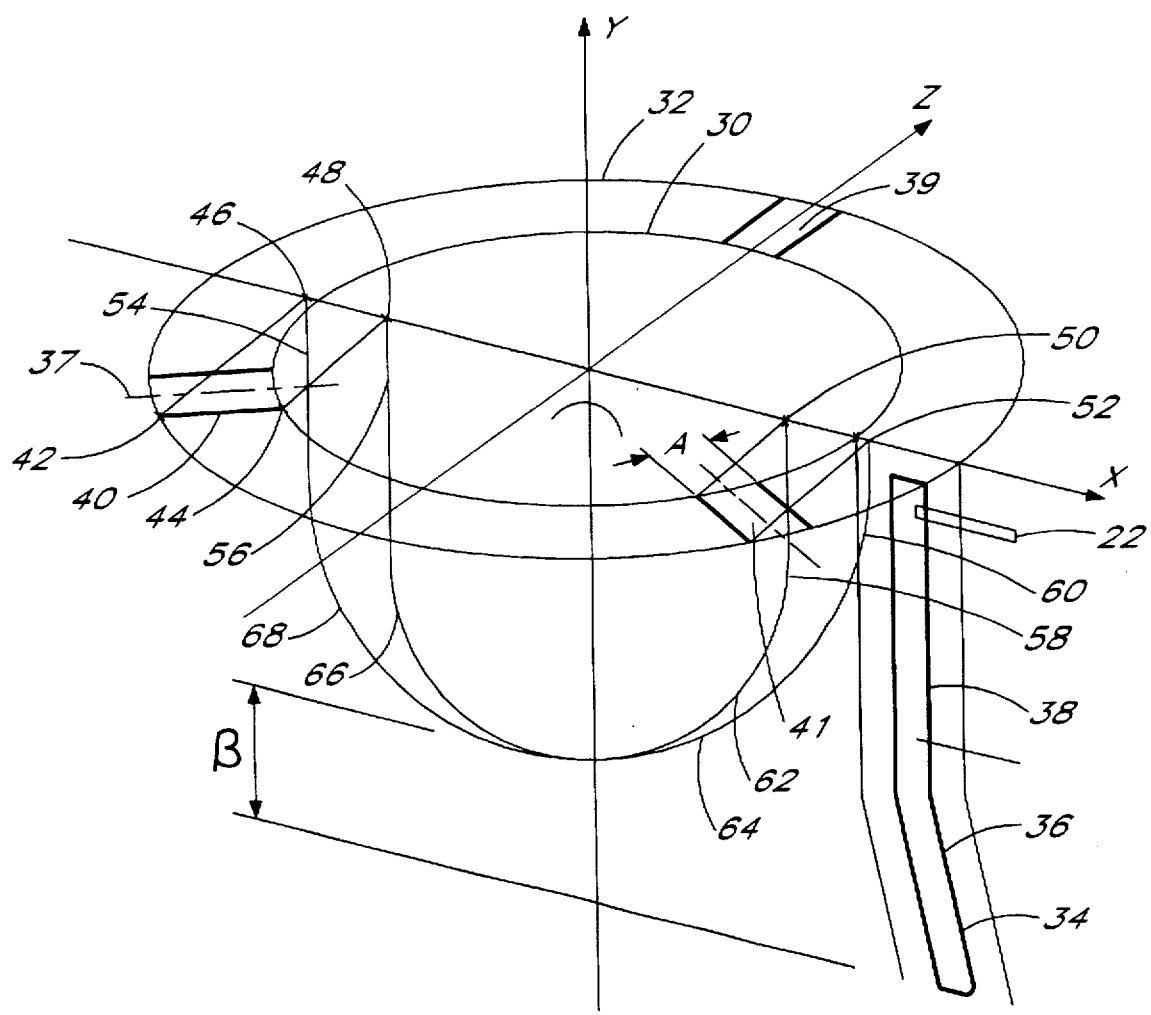
FIG. 2 is a view of the geometry of construction of the inner stent.

Referring to FIG. 2, which illustrates the construction of the inner stent basic geometry from these parameters, the designer, typically operating on a computer having CAD software, creates inner and outer circles 30 and 32 respectively in the x-z plane of the space in which the valve design will be created. A stent post primitive 34, which represents a cross section of the inner stent blank, is rotated about the y-axis to create the stent blank. The stent post primitive has a base section 36, which has a taper, typically approximately 15 degrees, and an upper section 38, to which the outwardly-projecting members 22 are attached. The upper section 38 is preferably parallel to the y axis. The taper helps bias the valve into a closed position, which enables the valve to close more easily in low-pressure conditions. It also produces a "jet nozzle" effect which reduces turbulence as blood flows through the valve, leading to a smaller net pressure drop across the valve and resulting in less energy loss to the cardiac cycle.

The stent post width is shown as dimension A in FIG. 2 and is drawn onto the annulus between the circles 30 and 32 at three equally-spaced intervals separated by 120 degrees, creating locations 37, 39, and 41, which represent the positions of the stent posts of the completed stent. In FIG. 2, posts 37 and 41 are shown spaced 30 degrees each from the x-axis to facilitate understanding of the construction process described below. For each post, such as 37, a vector, such as that shown at 40, is drawn from a point 42 at the intersection of the post edge closest (in the x-direction) to the center of the circles and the circle 32, to a point 44 corresponding to the intersection of the post edge closest (in the x-direction) to the center of the circles and the circle 30.

This vector is projected onto the x axis, forming a line having endpoints 46 and 48. This procedure is repeated for post 41, resulting in a projection having endpoints 50 and 52. The geometry of the scalloped edge separating posts 37 and 41 is determined from the points 46, 48, 50, and 52 that result from the projection operations described above as follows: vertical lines parallel to the y-axis, 54, 56, 58, and 60 are dropped from the respective points 46, 48, 50, and 52, and semicircles 62 and 64 are constructed to intersect, at their edges, the lines 50, 56, 54, and 60 respectively. The semicircles are constructed to be tangent to a line parallel to the x axis and spaced a distance β, the height of the scallop above the outer stent base, from the base of the stent primitive. The union of these semicircles and their respective vertical lines forms curves which will be referred to hereinafter as splines 66 and 68. As will be seen, these splines, when projected onto the surface of rotation formed with the stent primitive, determine the shape of the scalloped edge separating posts 37 and 41. The projection of vectors such as 40 onto the x-axis to create another vector lying in the x axis and having endpoints 46 and 48 is performed to ensure that the resulting splines, when projected onto the inner stent blank and ruled as described below, will form smooth surfaces intersecting the stent blank along their entire length. By rotating the inner stent about the y-axis by 120 degrees, an identical procedure may be used to construct the other two splines.

Figure 3:
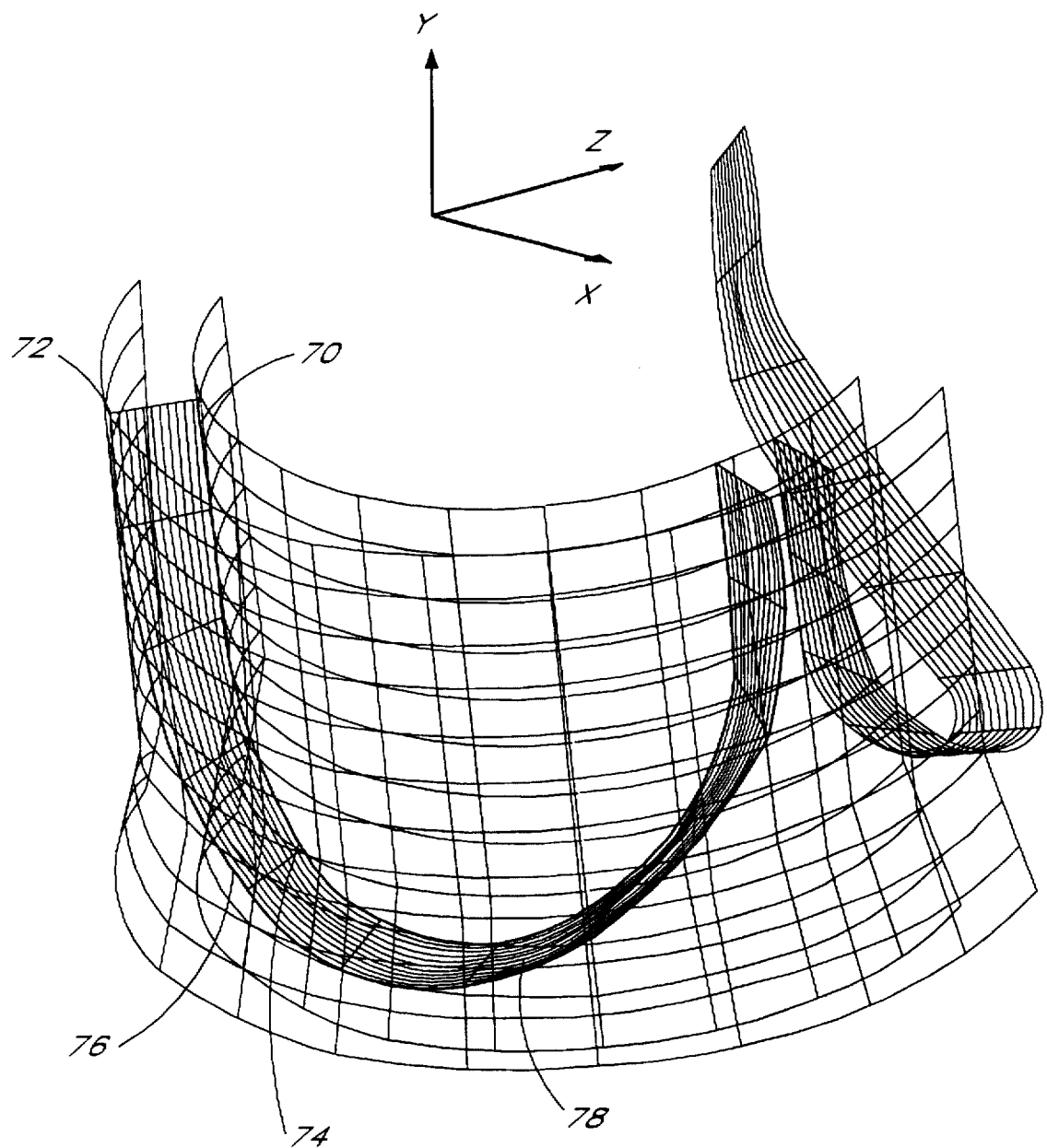
FIG. 3 is a wireframe view of a partially-constructed inner stent, particularly showing the scallop geometry.

As shown in FIG. 3, the three-dimensional solid model of the inner stent is created by revolving the inner stent post primitive 34 about the y-axis, thereby creating an inner surface 70 and an outer surface 72 of the inner stent. The inner spline 66 is then projected onto the inner surface 70 in three dimensions, and the outer spline 68 is projected onto the outer surface 72. The resulting spline curves 74 and 76 are thus functions of all three spatial variables.

Next, a ruled surface 78 connecting splines 74 and 76 is created. This ruled surface may be transformed into a b-surface containing many nodes by a suitable surface-fitting algorithm to more precisely define the scallop surface, if required by the particular CAD system employed in the design process. The ruled surface 78 or a similar b-surface represents the actual surface in space of the scallop connecting stent posts 37 and 41 and will eventually be sectioned out of the surface of revolution defining the solid model of the inner stent blank.

An important feature of the present invention is that the scallop profile is perpendicular to the axis of the stent, i.e. that a line connecting the inner and outer surfaces of the inner stent along the surface defining the scallop is always parallel to the x-z plane at all positions along the scallop. This feature permits the tissue, which is draped over the scallops, to contact the inner stent along its entire width, thereby preventing the formation of possible points of fatigue on the tissue.

Another advantageous feature of the present invention is that the inner stent is designed so that cusps of the valve are spherical sections. The arcs 62 and 64 are chosen to be circular because such a geometry results in a spherical configuration for each cusp of the heart valve. This spherical configuration is important in ensuring adequate stress distribution throughout the tissue comprising the valve leaflets.

After the creation of the ruled surface 78 between the stent posts 37 and 41, two other ruled surfaces constructed in an identical fashion to the ruled surface 78 are added between the other stent post 39 and the posts 37 and 41. These surfaces are used to form the scallops by splitting the solid model of the inner stent blank at their intersection with the solid inner stent model.

Figure 4:
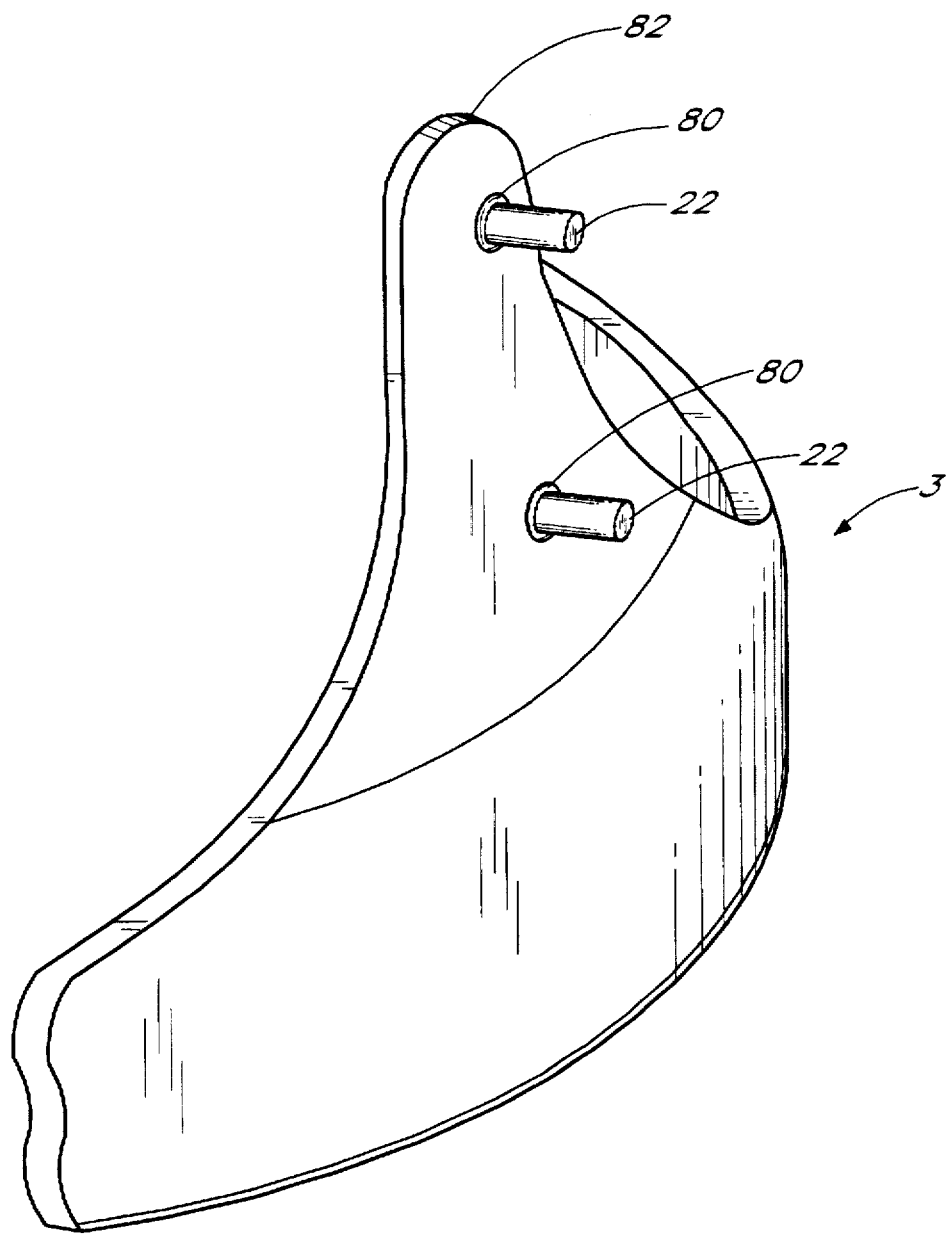
FIG. 4 is a perspective view of a portion of the inner stent.

The finished three-dimensional model of the inner stent, which is output to programmable tooling, is created by deleting the remaining surfaces and adding the fillets 80 and 82 to the inner stent posts, as shown in FIG. 4, to smooth the upper surfaces of each of the posts. The outward-facing tissue alignment members 22 are also added. Then, the programmable tooling is used to fabricate an electrode having a shape corresponding to that output by the CAD system. This electrode dissolves a pattern into a block of a suitable alloy into the proper shape to create the final injection mold for the inner stent.

The geometry of the outer stent 1 is determined much the same way as that of the inner stent 3 in the preferred embodiment of the present invention. Referring to FIG. 5, the outer stent post primitive 84 is created with a tapered portion 86 and a vertical portion 88. The lower portion of the outer stent primitive is displaced outwardly a suitable distance, typically 20 mils, from the location of the corresponding inner stent primitive 34, and the outer stent blank is revolved about the y-axis to create an outer stent solid model (not shown). As with the inner stent, the solid model is cut by calculated ruled or b-surfaces defining the scallops, and the required fillets are added to the final model. During the design of the external shape of the outer stent, the scalloped edges 90 are created somewhat differently from those of the inner stent, however.

Figure 6:
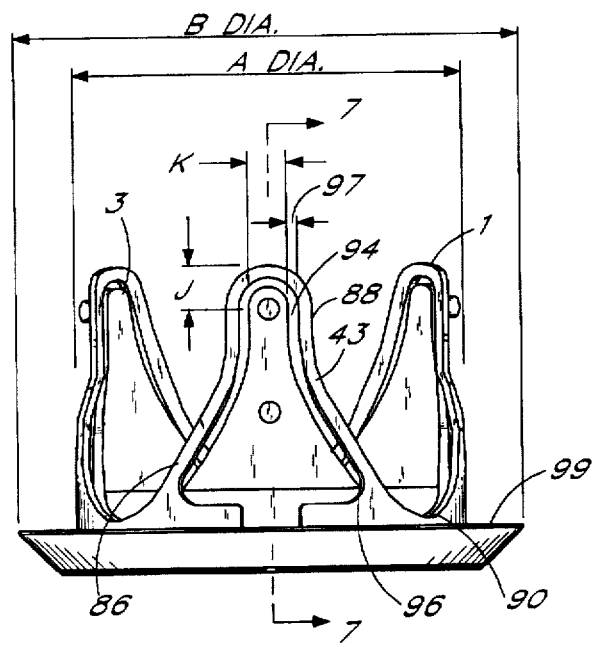
FIG. 6 is a side view of the bare inner stent inserted into the outer stent.
Figure 7:
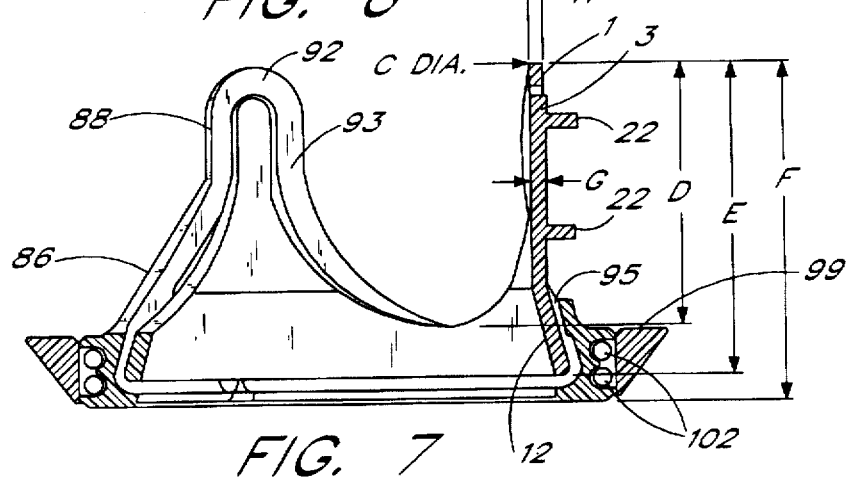
FIG. 7 is a cutaway view of the inner and outer stents mated together, showing the relevant clearances between the inner and outer stents.

An important objective in the design of the outer stent 1 is the maintenance of sufficient clearance between it and the inner stent 3 to prevent the tissue 2 wrapped around the inner stent from being pinched by the outer stent when the stents are mated together during the valve assembly process. Such pinching could lead to the formation of stress raisers in the tissue and ultimately result in tearing of the valve tissue. As seen in FIGS. 6 and 7, unwanted pinching could occur, for example, in the radially-outward direction at the base of both stents at location 95, between the posts of the inner stent and the windows 94 of the outer stent in both the radial and tangential directions at location 97, or anywhere in the volume formed between the inner and outer stents connecting these locations. It is thus important to provide sufficient clearance along the entire inner/outer stent mating region, which passes through these locations.

Figure 8:
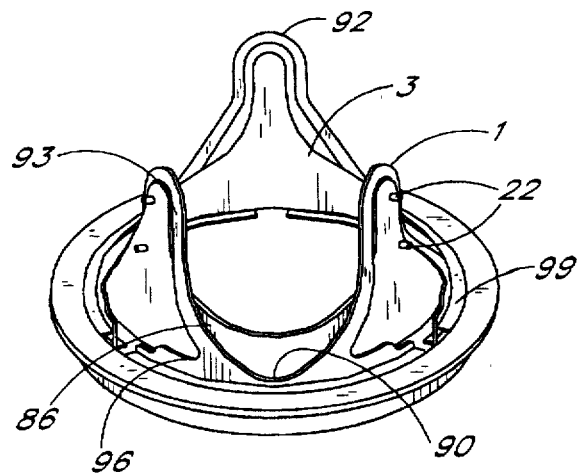
FIG. 8 is a perspective view of the mated inner and outer stents.
Figure 9:
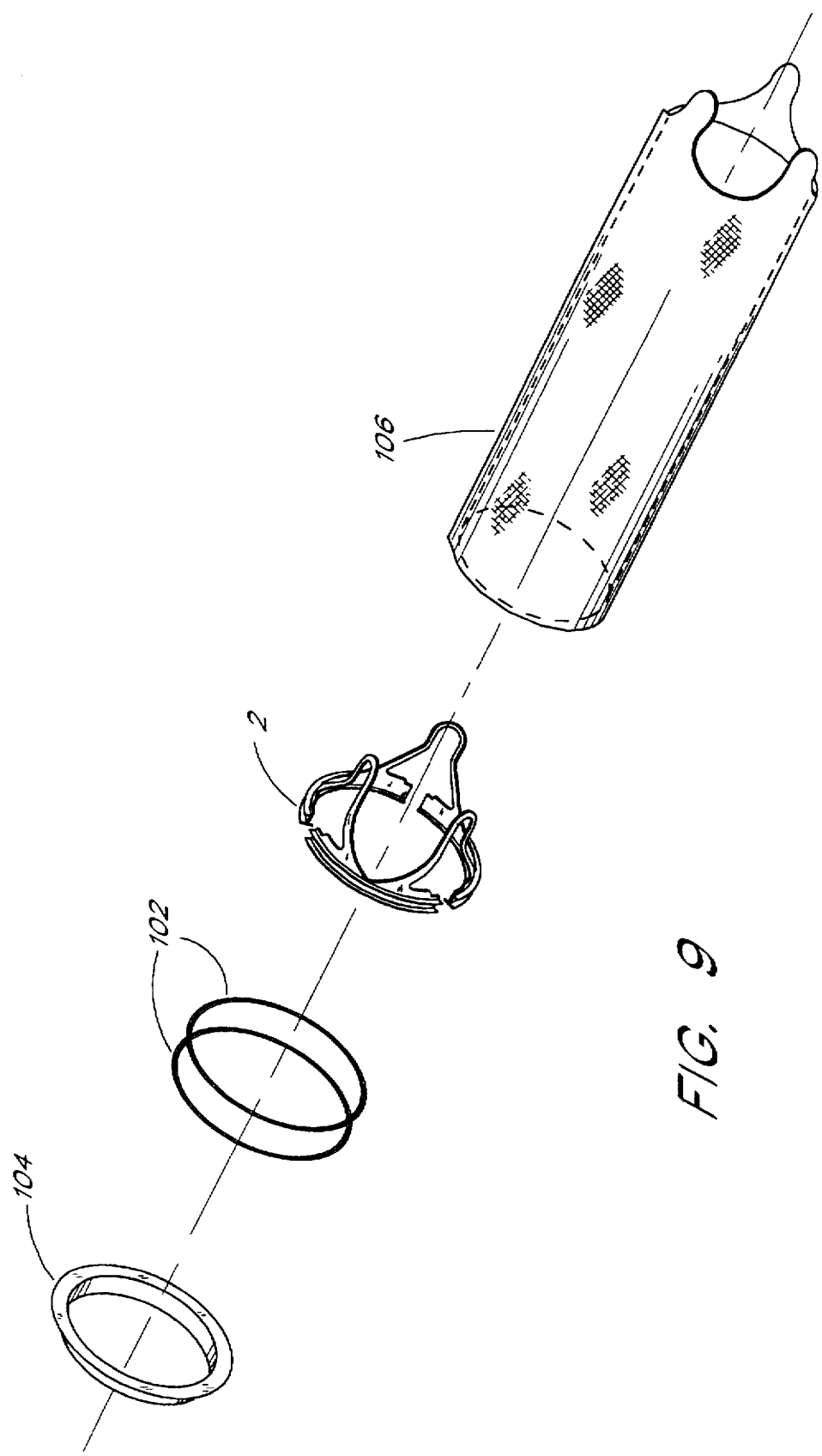
FIG. 9 is an exploded view of the outer stent, securing springs, and covering sock of the present invention.

The outer stent design must also simultaneously achieve the objective of providing sufficient strength to the posts 92 to withstand the wear the valve will be subjected to over the life of its user. Both of these objectives are advantageously realized by forming the window 94 into a spaded shape by including the fillet 96 and slightly deforming the ruled or b-surfaces used to create the outer stent scalloped edges to contain a cusp, as shown at numeral 90 in FIG. 8. The spaded window shape allows the outer stent posts to maintain sufficient clearance in both the tangential and radial directions with the inner stent posts and the tissue wrapped thereon, while the cusp-shaped scallop design imparts sufficient thickness to each of the struts 93 to provide the required strength to each post 92.

While the above-described method for designing the shapes of the inner and outer stents has proven satisfactory, it will be understood that the use of other techniques to determine the scallop and post geometry is possible as well.

The clearance required between the inner and outer stents along the mating surfaces, as at locations 95 and 97, is typically approximately 20 mils if a thin DACRON sock is used to cover the inner and outer stents, and tissue having a thickness of approximately 15 mils is used to fabricate the valve. Such a value for the clearance also allows the tissue to penetrate the interstices of the DACRON cover, resulting in less slippage between the tissue and the stents. Other dimensions for the inner and outer stents are identified with the letters A–K in FIGS. 6 and 7. These dimensions are proportional to the size of the annulus to be fitted with the valve. Table 1 shows the preferable relationship between these dimensions (in inches) and a variety of possible sizes of the annulus to be fitted:

| SIZE (MM) | A DIA | B DIA | C DIA | D | E | F | G | H | J | K |
|---|---|---|---|---|---|---|---|---|---|---|
| 17 | .641 | .895 | .482 | .299 | .373 | .454 | .022 | .021 | .085 | .049 |
| 19 | .708 | .992 | .540 | .342 | .419 | .506 | .025 | .021 | .090 | .054 |
| 21 | .773 | 1.079 | .592 | .378 | .460 | .553 | .027 | .023 | .092 | .060 |
| 23 | .844 | 1.180 | .650 | .414 | .505 | .606 | .030 | .025 | .103 | .060 |
| 25 | .915 | 1.277 | .708 | .450 | .549 | .657 | .033 | .027 | .115 | .069 |
| TOL. | −.040 | +.040 | −.005 | +.005 | +.005 | +.005 | +.002 | −.003 | +.005 | −.005 |

Other valve sizes are possible, such as valves configured for young children, where the annulus size might be as small as 14 mm.

The dimensions in Table 1 have proven to be acceptable in practice, and allow the formation of spherical cusps, which have the advantages described above, from the tissue 2 in the completed valve.

Figures 10, 11:
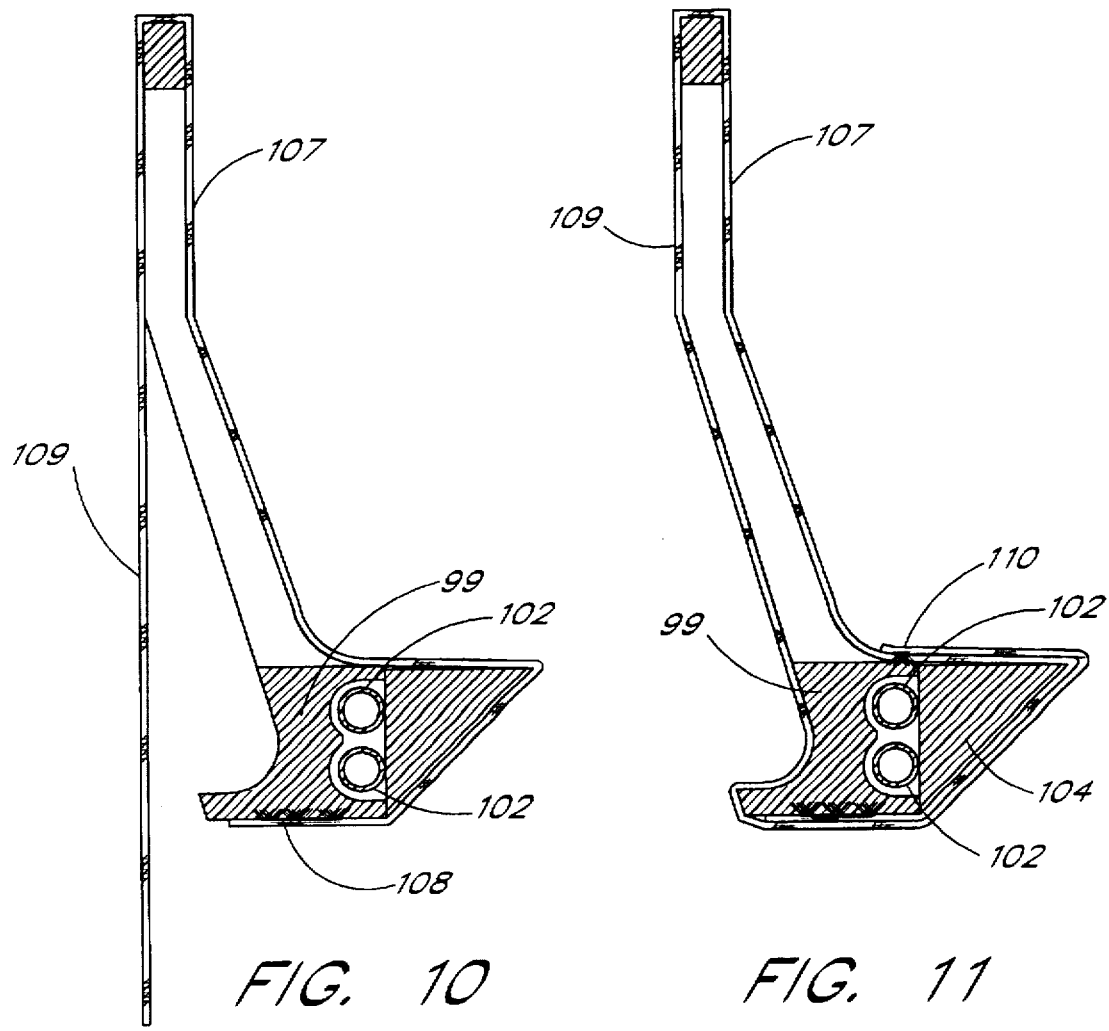
FIG. 10 is a cross section of a post of the outer stent, showing part of the process of covering the outer stent with a fabric sock.
FIG. 11 is a cross section of a post of the outer stent when fully covered with a fabric sock, showing the bonding of the fabric to the surface of the outer stent.
Figure 12:
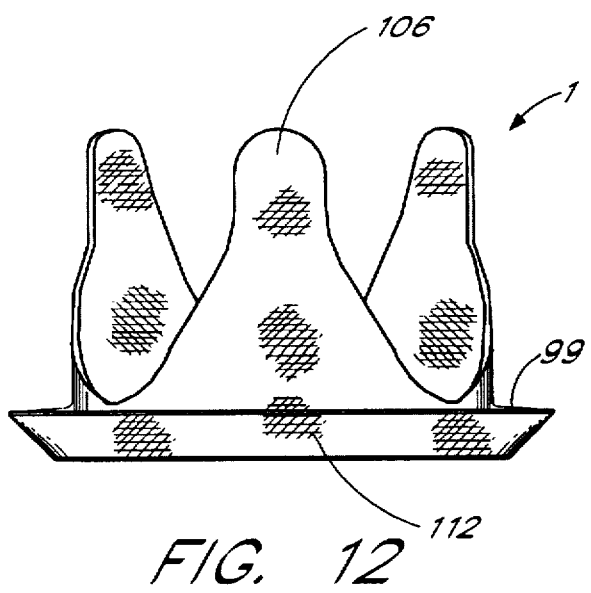
FIG. 12 a side view illustrating the placement of adhesive between the fabric layers covering the outer stent.

Other features incorporated into the outer stent are illustrated in FIGS. 10–11. In the preferred embodiment, the base 99 of the outer stent is provided with a plurality of garter springs 102 or other securing members extending around the length of its base. The garter springs 102 provide the tension force which secures the inner and outer stents together. More than one garter spring is advantageously used in the present invention to increase the redundancy of the valve. If one garter spring breaks, the presence of another spring ensures that the outer stent is still able to fulfill its role of clamping the tissue around the inner stent. Such a result would not be possible if only one spring is used around the base of the outer stent.

Another advantageous feature of the present invention is the provision of a wedge-shaped sewing ring 104, which is attached to the annular base of the outer stent. The sewing ring 104 provides a site on the valve assembly for securing it into the patient's annulus by use of sutures or similar means. A wedge-shaped sewing ring has been found to fit better into the aortic root of a patient than other shapes when the valve is used as an aortic replacement.

As shown in FIGS. 9–12, the outer stent is covered with a DACRON sock 106. Covering the stent frame accomplishes the purpose of isolating nonbiological material, such as the stent frame thermoplastic, from the body. This also helps avoid the problem of thromboembolism, which occurs with the use of mechanical valves. It also accomplishes the purpose of promoting tissue ingrowth into the interstices of the fabric, to further isolate the nonbiological material from the body, and integrate the valve into the heart. Additionally, it accomplishes the purpose of providing an interface to the tissue clamped between the stents which is gentle, and which helps nourish the tissue and promote its viability by allowing free passage of blood to the tissue.

To cover the outer stent frame, first, a three-fingered DACRON sock is formed by heat seaming inner and outer sections of DACRON fabric together utilizing either hot wire or ultrasonic techniques. Alternatively, the sock can be woven as one piece or sewn. The sock is then pulled over the outer stent frame and its outer section 107 is secured at the outer stent base at weld 108. Next, the sock's inner section 109 is wrapped around the inner surface of the outer stent, as well as around the outer stent base itself. The inner layer is secured to the top of the base at a second weld 110. The use of these two welds on the outer stent base advantageously provides two layers of fabric covering extending along the entire circumference of the outer stent base and thus increases the resilience of the base. Additionally, this method of securing the DACRON sock also achieves the object of isolating the securing weld 108 from the patient's bloodstream, minimizing the risk that blood clots would form on the weld and enter the patient's bloodstream.

Along the portions of the outer stent base having slots, it is not possible to bond the inner section of the DACRON sock 106 to the upper surface of the base 99. Nevertheless, it is desirable to bond the inner and outer sections of the sock to each other at these locations to prevent the separation of these sections and the possibility of thromboemboli formation. Consequently, the present invention advantageously utilizes a medical-grade adhesive, such as RTV silicone adhesive, to secure the outer and inner sections of the sock together along segments such as 112. Adhesive is applied to the inner or outer section along the portions of the outer stent base overlying a slot.

While embodiments and applications of this invention have been shown and described, it should be apparent to those skilled in the art that many more modifications are possible without departing from the scope of the present invention. The invention is therefore not to be restricted, except in the spirit of the appended claims.

What is claimed is:

1. An outer stent for securing an inner stent having a base and a plurality of posts extending therefrom and spaced around the base and tissue wrapped thereon, said outer stent spreadable from a relaxed position to a spread position, said outer and inner stents cooperating to form a heart valve implanted into a patient by use of sutures and needles, said outer stent comprising:

a base having a plurality of slots;
a tensioning spring disposed around said base;
a plurality of posts extending upwardly from said base, said posts adapted to register with said inner stent when said inner and outer stents are secured together, at least one of said posts including a window to allow the insertion of the posts of said inner stent therein;
an elastic ring disposed around said base for allowing the securing of said outer stent to said patient; and
a covering emplaced around said base and said posts and bonded to said base at a plurality of locations.

2. The outer stent of claim 1 further comprising a plurality of scalloped portions disposed between said posts.

3. The outer stent of claim 2 wherein each of said scalloped portions contains a cusp at its midsection.

4. The outer stent of claim 1 wherein said posts and said base are shaped so as to prevent said tissue from being pinched when said inner stent has been inserted into said outer stent.

5. An outer stent for securing an inner stent having a base and a plurality of posts extending therefrom and spaced around the base and tissue wrapped thereon, said outer stent spreadable from a relaxed position to a spread position, said outer and inner stents cooperating to form a heart valve implanted into a patient by use of sutures and needles, said outer stent comprising:

a base having a plurality of slots;
a tensioning spring disposed around said base;
a plurality of posts extending upwardly from said base, said posts connected by scalloped portions, said posts adapted to register with said inner stent when said inner and outer stents are secured together, each of said posts including a window to allow the insertion of the posts of said inner stent therein;
an elastic ring disposed around said base for allowing the securing of said outer stent to said patient; and
a covering emplaced around said base and said posts and bonded to said base at a plurality of locations.

6. An outer stent for securing an inner stent having a base and a plurality of posts extending therefrom and spaced around the base and tissue wrapped thereon, said outer stent spreadable from a relaxed position to a spread position, said outer and inner stents cooperating to form a heart valve implanted into a patient by use of sutures and needles, said outer stent comprising:

a frame having an annular lower portion and an upper portion, said lower portion having a plurality of slots, said upper portion integrally formed with and extending upwardly from said lower portion to form a plurality of posts, at least one of said posts having a window to allow the insertion of the posts of said inner stent therein;
a tensioning spring disposed in a circumferential groove formed in an outer surface of said lower portion, said spring causing said lower portion of said frame to clamp said tissue between said inner and outer stents when formed as said heart valve;
an elastic ring disposed around said lower portion for allowing the securing of said outer stent to said patient; and
a covering emplaced around said frame and said ring and bonded to said lower portion of said frame at a plurality of locations.

7. An outer stent for securing an inner stent having a base and a plurality of posts extending therefrom and spaced around the base and tissue wrapped thereon, said outer stent spreadable from a relaxed position to a spread position, said outer and inner stents cooperating to form a heart valve implanted into a patient by use of sutures and needles, said outer stent comprising:

a base having a plurality of slots;

a tensioning spring disposed in a groove formed around said base for providing a radially compressive force about said base and configured to clamp said tissue between said inner and outer stents when formed as said heart valve;

a plurality of posts extending upwardly from said base, said posts adapted to register with said inner stent when said inner and outer stents are secured together, at least one of said posts including a window to allow the insertion of the posts of said inner stent therein;

an elastic ring disposed around said base for allowing the securing of said outer stent to said patient; and a covering emplaced around said base and said posts and bonded to said base at a plurality of locations.

* * * * *